United States Patent [19]
>
> Trijzelaar et al.

[11] 4,442,107

[45] Apr. 10, 1984

[54] QUINOLINE DERIVATIVES, PHARMACEUTICAL COMPOSITIONS CONTAINING SUCH COMPOUNDS, AND METHODS FOR TREATING CARDIOVASCULAR CONDITIONS WITH THEM

[75] Inventors: Hans B. Trijzelaar, Zeist; Ronus de Bode, Bilthoven; Hendricus B. A. Welle, Maarssen, all of Netherlands

[73] Assignee: ACF Chemiefarma N.V., Netherlands

[21] Appl. No.: 240,818

[22] Filed: Mar. 5, 1981

[30] Foreign Application Priority Data

Mar. 6, 1980 [NL] Netherlands ............... 8001369
Jul. 11, 1980 [NL] Netherlands ............... 8004003

[51] Int. Cl.³ ................. A61K 31/47; C07D 401/06
[52] U.S. Cl. ................................... 424/258; 546/156; 546/157; 546/168; 546/174; 546/176; 546/177
[58] Field of Search ............ 546/156, 157, 176, 177, 546/174, 168; 424/258

[56] References Cited

U.S. PATENT DOCUMENTS

| 3,914,235 | 10/1975 | Gutzwiller et al. | 424/258 X |
| 3,953,453 | 4/1976 | Grethe et al. | 546/134 |
| 4,237,139 | 12/1980 | Champseix et al. | 424/258 |
| 4,238,612 | 12/1980 | Barieux et al. | 546/153 |
| 4,299,835 | 11/1981 | Champseix et al. | 424/258 |

FOREIGN PATENT DOCUMENTS

| 31753 | 7/1981 | European Pat. Off. | 424/258 |
| 2315148 | 10/1973 | Fed. Rep. of Germany . | |
| 2206944 | 6/1974 | France | 546/176 |

OTHER PUBLICATIONS

Grethe, et al., Chemical Abstracts, vol. 83, 114,718j (1975).
Heidelberger, et al., J. Am. Chem. Soc., vol. 44, pp. 1098–1107 (1922).
Wirth, Chemical Abstracts, vol. 76, 103776f (1972).
Wirth, Chemical Abstracts, vol. 80, 124762w (1974).
Dawes, British J. Pharmacol., 1, pp. 90–111 (1946).

Primary Examiner—Donald G. Daus
Assistant Examiner—Diana G. Rivers
Attorney, Agent, or Firm—Jacobs & Jacobs

[57] ABSTRACT

The invention is concerned with quinoline derivatives having cardiovascular activities of the formula

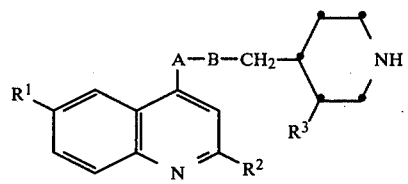

or a salt thereof, in which A—B is —$CH_2$—$CH_2$—, —CHOH—$CH_2$—, —$CH_2$—CHOH—, —C(O)—$CH_2$—, —$CH_2$—C(O)—, —C($NOR^4$)—$CH_2$—$CH_2$— or —$CH_2$—C($NOR^4$)—, $R^1$ is hydrogen, hydroxy or lower alkoxy, $R^2$ is hydroxy, lower alkoxy, trifluoromethyl, $R^3$ is ethyl or vinyl and $R^4$ is lower alkyl. The compounds of the formula may be in the form of their optically active enantiomers and/or their therapeutically acceptable salts. Furthermore the invention provides pharmaceutical compositions possessing cardiovascular activities, in which as active compound at least a compound of the above formula is used. Methods for the preparation of the pharmaceutical compositions and of the active compounds are also disclosed and covered by the invention.

14 Claims, No Drawings

QUINOLINE DERIVATIVES, PHARMACEUTICAL COMPOSITIONS CONTAINING SUCH COMPOUNDS, AND METHODS FOR TREATING CARDIOVASCULAR CONDITIONS WITH THEM

The invention relates to quinoline derivatives and pharmaceutical compositions containing such compound.

French Pat. No. 73,41043 (Publ. No. 2,206,944) discloses quinoline derivatives of the formula:

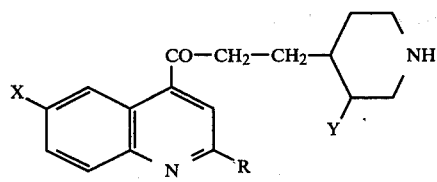

in which
X is hydrogen or methoxy,
Y is hydrogen, ethyl or vinyl and
R is $C_{1-4}$ alkyl, cycloalkyl or optionally substituted aralkyl or aryl, which compounds may be used for the treatment and prophylaxis of cardiovascular affections.

From Ann. Pharm. Fr. 24, 39 (1966) the pharmacodynamic properties of quinicine which chemically is 1-(6-methoxy-4-quinolyl)-3-(3-vinyl-4-piperidyl)-1-propanone, also named viquidil, are known, in particular in the field of CNS, and the hypotensive, vasodilative and anti-spasmodic activities.

In British Pat. No. 1,294,538 the use of viquidil in the treatment of cerebral vessel injury, cerebrovascular insufficiency and memory deficiency in humans is described.

In Dutch Patent Application No. 77,06614 quinoline derivatives are described of the formula:

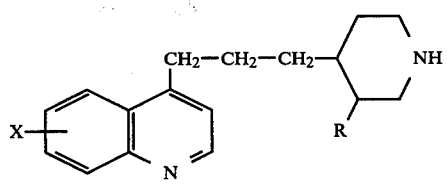

in which
R is hydrogen, $C_{1-4}$ alkyl or $C_{2-4}$ alkenyl and
X is hydrogen, halogen, $C_{1-4}$ alkyl, alkoxy or alkylthio, trifluoromethyl, nitro, hydroxy, an amino group optionally substituted by one or two $C_{1-4}$ alkyl groups, or $C_{1-4}$ acyl or alkylsulfonyl group, which compounds have a serotonin uptake inhibiting effect and anti-arrhythmic activity.

The German Patent Application DT No. 2,949,993 discloses compounds of the formula:

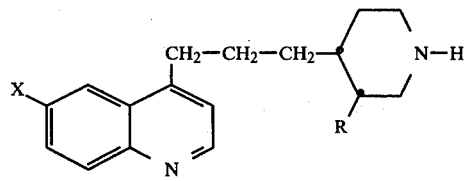

in which
R and X are both H, or R is vinyl or ethyl, and
X is H or methoxy.

Said compounds are used for the treatment of anxiety.

U.S. Pat. Nos. 3,873,549 and 3,914,235 describe compounds of the formula:

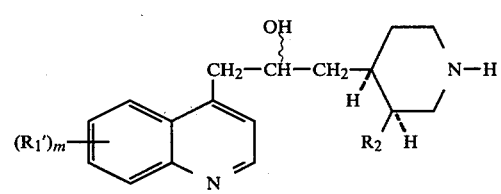

and their antipodes and racemates, in which m is 0, 1 or 2; $R_1'$ is OH, halogen, $CF_3$, methyl, ethyl, propyl, butyl or methoxy or, when m is 2, $R_1'$ with adjacent $R_1'$ may also be methylenedioxy, and $R_2$ is vinyl or ethyl, are described as intermediates for quinine and quinidine compounds of known use as anti-malarials and anti-arrhythmics, whereas such componds showed bactericidal activity.

In U.K. Pat. No. 1,441,519 compounds of formulae 12 and 13

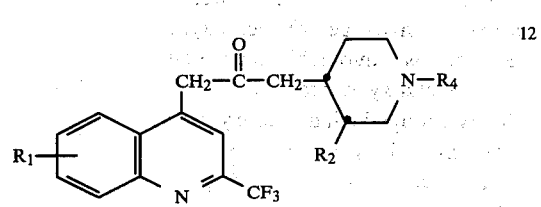

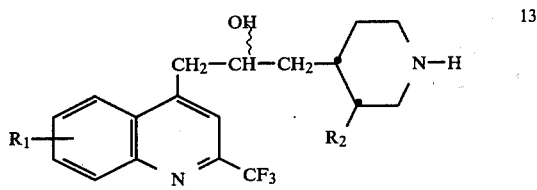

with $R_1$ is halogen or $CF_3$, $R_2$ is ethyl or vinyl and $R_4$ is hydrogen or lower alkanoyl, are mentioned as intermediates.

It has now been found, that quinoline derivatives substituted at the 2- and 4-position and optionally at the 6-position, and in which the substituent at the 4-position contains a 3,4-disubstituted piperidyl group, possess unexpected pharmacological properties, namely desirable effects on the cardiovascular system such as antihypertensive, anti-thrombotic, vasodilatory and antiarrhythmic activity. The compounds are particularly useful in medicines administered for the treatment of hypertensive or arrhythmic conditions.

Thus, the invention provides compounds of formula 1

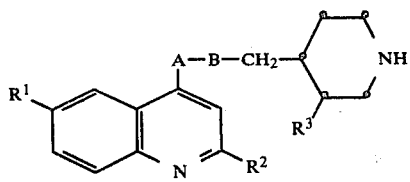

in which
A–B is —CH₂—CH₂—, —CHOH—CH₂, —CH₂—CHOH—, —C(O)—CH₂—, —CH₂—C(O)—, —C(NOR⁴)—CH₂—CH₂— or —CH₂—C(NOR⁴),
R¹ is hydrogen, hydroxy or lower alkoxy,
R² is hydroxy, lower alkoxy or trifluoromethyl,
R³ is ethyl or vinyl,
R⁴ is lower alkyl,
whereby the substituents at the 3- and 4-position of the piperidine ring are in the cis configuration, and acid addition salts thereof.

As is usual, the carbon chains of the different groups may be straight or branched.

The term "lower" is here used to mean a group with up to six carbon atoms.

Suitably, A–B is —CH₂—CH₂—. Another suitable meaning of A–B is —CHOH—CH₂—. Also suitable is the meaning of A–B being —CH₂—CHOH—. Suitably, A–B is —C(O)—CH₂. Also suitably, A–B is —CH₂—C(O)—. The meaning of A–B being —C(NOR⁴)—CH₂ is also apt, as well as A–B being —CH₂—C(NOR⁴)—, R⁴ being preferably methyl.

Where R¹ is alkoxy, it is preferably methoxy. R¹ is preferably hydrogen or methoxy, favourably R¹ is hydrogen. Also favourably R¹ is methoxy.

R² as alkoxy is preferably methoxy. Other suitable alkoxy groups include ethoxy, n-propoxy, isopropoxy, n-butoxy and n-pentoxy.

Also suitable is the meaning of R² being hydroxy. Also suitable is the meaning of R² being trifluoromethyl.

Our copending application Ser. No. 240,808 filed Mar. 5, 1981, describes compounds of the formula:

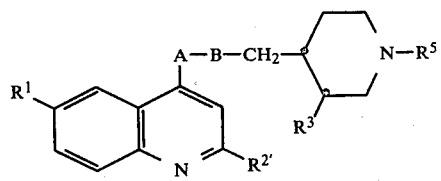

in which
A–B, R¹ and R³ have the same meanings as the compounds of formula 1,
R²' is lower alkyl, hydroxy or lower alkoxy, and
R⁵ is a substituent other than hydrogen,
which compounds possess certain cardiovascular properties.

A particular group of compounds of formula 1 are those of formula 1a

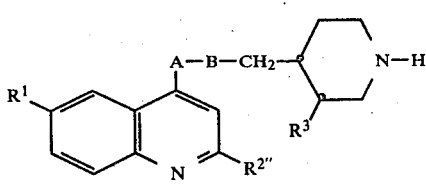

in which
A–B, R¹ and R³ are as defined above and
R²" is hydroxy or lower alkoxy.

Also a particular group of compounds of formula 1 are those of formula 1b

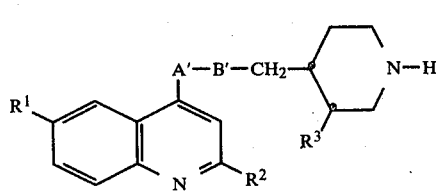

in which
R¹, R² and R³ are as previously defined and
A'–B' is —CH₂—CH₂—, —CHOH—CH₂—, —CH₂—CHOH, —C(NOR⁴)—CH₂— or —CH₂—C(NOR⁴).

Another group of favourable compounds of formula 1 are those of formula 1c

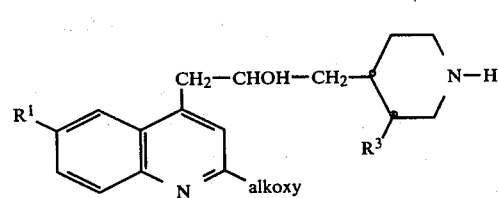

in which R¹ and R³ are as defined above. Of this group R¹ is preferably hydrogen or methoxy, especially hydrogen and R³ is ethyl, while the alkoxy group is preferably methoxy.

A further group of suitable compounds of formula 1 are those of the formula 1d

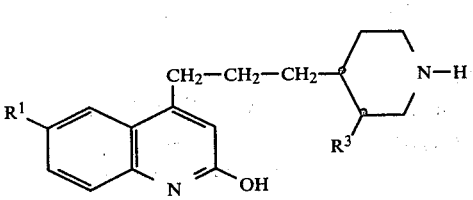

in which R¹ and R³ are as previously defined. Preferably, R¹ is hydrogen and R³ is ethyl.

Another group of particular compounds of formula 1 are those of formula 1e

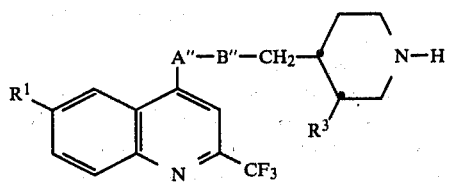

1e in which
$R^1$ and $R^3$ are as previously defined and
A''-B'' is —CH$_2$—C(O)— or —CH$_2$—CHOH. Preferably $R^1$ is hydrogen and $R^3$ is ethyl.

A further group of suitable compounds of formula 1 are those in which A-B is —CH$_2$—CHOH—, $R^1$ is hydrogen, $R^2$ is trifluoromethyl and $R^3$ is ethyl including both separated diastereoisomers and the mixture of the two diastereoisomers.

Another group of suitable compounds of formula 1 are those of formula 1f

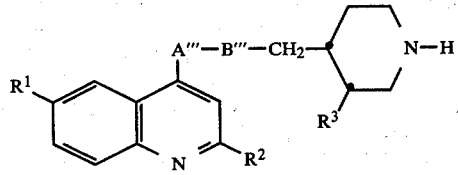

1f in which A'''-B''' is —C(NOR$^4$)—CH$_2$ or —CH$_2$—C(-NOR$^4$)— and $R^1$, $R^2$, $R^3$ and $R^4$ are as previously defined. Preferably, $R^4$ is methyl.

The preceding compounds of formula 1 may exist in free base form or in the form of their acid addition salts, for example their salts with mineral acids, e.g. hydrochloric acid, hydrobromic acid or sulphuric acid, or organic acids, e.g. acetic acid, fumaric acid or tartaric acid. Naturally the acid used will be pharmaceutically acceptable when such salts are intended for internal administration.

The compounds of formula 1 in which A or B is —CHOH— contain an asymmetric carbon atom and therefore two stereoisomers may exist, provided that there are no asymmetric carbon atoms in a side chain.

The compounds of the invention are obtainable in crystalline form. They may also be obtained in the form of solvates such as hydrates.

The compounds of the invention, as represented by formula 1, include free base and acid addition salt forms, mixtures of diastereoisomers and separated forms thereof.

In most cases the compounds of the invention may be prepared analogous to the synthesis of known compounds.

Compounds of formula 1, in which $R^2$ is alkoxy and A-B is a —C(O)—CH$_2$—group, may be obtained by quaternizing a compound of the formula:

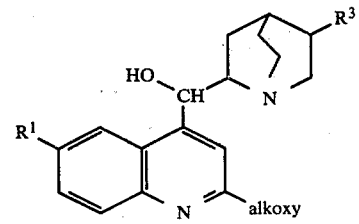

2 in which $R^1$ and $R^3$ have the previously defined meanings, and converting this compound with a base.

The starting compounds of formula 2 are either known or may be obtained in analogous manner from known compounds. A suitable method for preparing these starting compounds is for example the conversion of a compound of formula

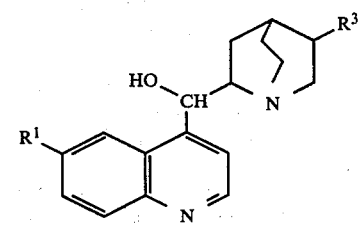

3 in which $R^1$ and $R^3$ are as defined above to the corresponding ar-mono-N-oxide in conventional manner, followed by conversion of the resulting compound e.g. with phosphoroxytrichloride to a cinchona alkaloid which is substituted at the 2'-position by chlorine, which compound may be converted with a suitable alkoxide to the corresponding 2'-alkoxy compound. Hydrolysis of the 2'-chloro compound affords directly the 2'-hydroxy compound. The starting 2'-unsubstituted cinchona alkaloid of formula 7 is preferably unsubstituted at the 6'-position or substituted by a methoxy group.

The compounds of formula 1 thus obtained, in which $R^2$ is alkoxy and A-B is —C(O)—CH$_2$— may be converted in conventional manner by complete or partial reduction to the corresponding —CH$_2$—CH$_2$— or —CHOH—CH$_2$— compounds respectively. A suitable reducing agent for the conversion to the desoxo compound (—CH$_2$—CH$_2$—) is e.g. hydrazine hydrate, in the presence of an alkali metal hydroxide, such as potassium hydroxide, in a suitable solvent such as an alcohol, e.g. ethylene glycol. A suitable reducing agent for the partial reduction to the alcohol derivative (—CHOH—CH$_2$—) is for example a complex hydride, such as sodium borohydride. This reduction is advantageously carried out at a temperature of about $-5°$ to $-10°$ C. in a suitable solvent, like an alcohol, e.g. isopropylalcohol. If desired, the alcohol compound may also be converted into the corresponding desoxo compound, e.g. by converting the alcohol in a suitable solvent, such as tetrachloromethane, with phosphorus pentachloride to the chloride and reducing the resulting compound, for example with hydrogen gas in a solvent, such as ethylalcohol and for example palladium on coal as a catalyst.

Compounds of formula 1 in which $R^2$ is alkoxy and A-B is —CH$_2$—CHOH—, may be prepared e.g. by reduction of a cis- or trans-oxirane compound of the formula:

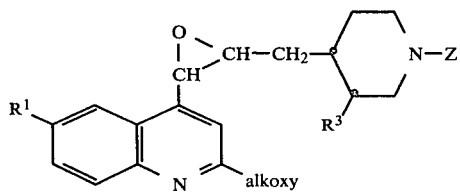

in which $R^1$ and $R^3$ are as defined above and Z is a protecting group and preferably benzyl, followed by removal of this protecting group on conventional manner. The reduction is suitably carried out by leading hydrogen gas through a suitable solvent, such as an alcohol, e.g. ethylalcohol, in the presence of a suitable catalyst, e.g. palladium on coal, at room temperature or slightly elevated temperature. As a result of the reduction generally alcohols are formed as a mixture of diastereoisomers, which may be separated in conventional manner. The removal of the protecting group may be carried out with known techniques. If the protecting group is alkyl, this group may be removed e.g. with cyanogen bromide or chlorocarbonic acid ester. If the protecting group is a benzyl group, debenzylation occurs preferably catalytically.

The preparation of these cis- and trans-oxirane compounds of formula 4 occurs analogous to the method described by L. Keefer, Thesis Univ. of New Hampshire 1966 and G. G. Lyle and L. K. Keefer, Tetrahedron 23, 3253–3263 (1967). Generally, the compounds may suitably be prepared by quaternizing a compound of formula 2 in conventional manner, for example to the corresponding benzo-bromide and converting the resulting compound with a base.

Because of the stereospecificy of the reaction a compound of formula 2 in the erythro configuration is preferably used as the starting material, while the quaternizing group is not too small, i.e. larger than methyl and ethyl. Thus- a suitable group is for example benzyl. The reaction with the quaternary compound is suitably carried out with a base, such as potassium hydroxide in a solvent, such as ethylalcohol.

It is noted, that if the above-described reaction is carried out with the quaternary salt of a threo compound of formula 2, a keto compound of the formula may be formed

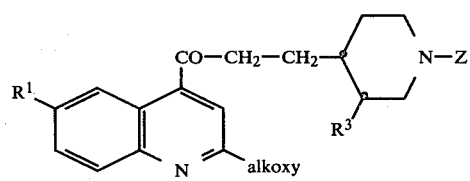

in which $R^1$, $R^3$ and Z are as previously defined. If a relatively small quaternizing group is used, such as a methyl group, generally a keto compound of formula 5 is formed in this reaction, both if a threo or an erythro compound of formula 2 is the starting material. Therefore, this method is also suitable for the preparation of compounds of formula 1, in which A–B is —C-(O)—CH$_2$—, in which naturally the protecting group Z has to be removed.

Threo compounds of formula 2 may also be converted to oxirane compounds of formula 4, if the quaternizing group is not too small, e.g. benzyl. This reaction is carried out with a strong base, in which the anion B$^-$ is bulky group, for example potassium t-butoxide in t-butanol. The resulting oxirane compound is usually in the cis-configuration.

The resulting compounds of formula 1, in which $R^1$ and $R^3$ are as previously defined, $R^2$ is alkoxy and A–B is —CH$_2$—CHOH—, may be oxidized in conventional manner to the corresponding keto compounds, in which A–B is —CH$_2$—C(O)—. A suitable method includes the Oppenauer oxidation. Such keto compounds may also be prepared by the cited second method from French Pat. No. 73,41043 or the method described in J. Amer. Chem. Soc. 100, 576–581 (1978), for example by condensing 4-methylquinoline which is substituted at the 2-position and optionally substituted at the 6-position with an ester of a 4-piperidylacetic acid derivative under the influence of lithium and a strong base. While removing a possible N-benzoyl group of the resulting keto compounds of the 1,3-disubstituted propanone-2 type, the compound is generally reduced to a propanol-2 derivative.

It is noted that the 2'-alkoxy group is easily converted to a 2'-hydroxy group under the influence of diluted acid. For the preparation of 2'-hydroxy compounds of formula 1 the corresponding 2'-alkoxy compound is therefore the preferred starting compound. It will also be appreciated, that 2'-hydroxy compounds may be easily converted to 2'-alkoxy compounds, for example by converting the hydroxy group with a solution of alkali hydroxide to an alkali salt and treating this compound with a dialkyl sulphate.

Compounds with formula 1, in which $R^2$ is hydroxy, may be also prepared starting from the corresponding 2'-unsubstituted compounds, e.g. by converting these compounds with m-chloroperbenzoic acid to the ar-mono-N-oxide, converting the resulting compound for example with phosphoroxytrichloride to the 2'-chloro compound and hydrolyzing this compound. It is noted that, if is started with a 2'-unsubstituted compound in which A or B is a carbonyl group, this group must be protected, for example by converting it to a ketal or thioketal according to conventional methods. It will be appreciated to those skilled in the art that in the same way also a 2'-alkoxy group may be introduced in compounds of formula 1 or 3, which is unsubstituted at the 2'-position.

Compounds of formula 1, in which $R^2$ is trifluoromethyl, may be also prepared by the above-described condensation method, for example by condensating 4-methyl-2-trifluoromethylquinoline which may be optionally substituted at the 6-position, with an ester of a 4-piperidylacetic acid derivative under the influence of lithium and a strong base. A suitable ester is for example the ethyl ester of (3-ethyl-4-piperidyl)acetic acid, in which the substituents are in the (3R, 4S) configuration. In order to reach or to retain this configuration it is recommended to prepare the compound by degrading a cinchona alkaloid such as quinine or cinchonidine.

The propanone-2 compound so obtained may be reduced in conventional manner to the propanol-2 compound, e.g. with sodium borohydride, resulting usually into a mixture of 2 diastereoisomers. This mixture may be separated by conventional means, e.g. by column chromatography.

The propanone-2 compound may be also converted to the corresponding desoxo compound, e.g. with hydrazine hydraat/potassium hydroxide.

Said propanol-2 compound may be also prepared by condensating (N-benzoyl-3-ethyl-4-piperidyl)acetaldehyde and 4-methyl-2-trifluoromethylquinoline, which is optionally substituted at the 6-position, in the presence of a base, followed by N-debenzoylation, for example with diluted sulphuric acid or diisobutyl aluminium hydride. Also in this case usually a mixture of diastereoisomers is obtained, which may be separated in conventional manner. For example, the aldehyde may be prepared by reducing the afore-described 4-piperidylacetic acid ester with diisobutyl aluminium hydride.

Compounds of formula 1, in which $R^2$ is trifluoromethyl or alkoxy and A–B is —C(O)—$CH_2$— or —CHOH—$CH_2$— respectively may be prepared in an analogous way by reacting a 4-halogenoquinoline which is substituted at the 2-position with a trifluoromethyl- or alkoxy group and which may be optionally substituted at the 6-position, with an ester of a (4-piperidyl)-propionic acid derivative or with a (4-piperidyl)-propionaldehyde derivative of the formula:

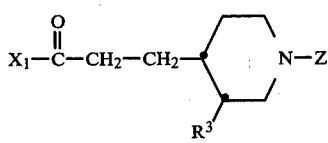

6 under the influence of lithium and a strong base.

In formula 6 $R^3$ is vinyl or ethyl, $X^1$ is alkoxy or hydrogen and Z is a protective group to be removed after the reaction.

The starting compounds of formula 1, in which A–B is —C($NOR^4$)—$CH_2$ or —$CH_2$—C($NOR^4$)—, may be obtained for example by reacting the corresponding carbonyl compound with an O-substituted hydroxylamine derivative of formula $R^4O$—$NH_2$, in which $R^4$ is as previously defined. This reaction is carried out in conventional manner for this type of reaction. Preferably, the reaction is carried out in a solvent, such as an alcohol, dioxane, dimethyl formamide or pyridine, at a temperature generally between room temperature and the boiling point of the reaction mixture. The hydroxylamine derivative is usually added as an acid salt, preferably the hydrochloride, which salt is preferably dissolved in pyridine.

The starting compounds which are necessary for the preparation of the compounds of the invention are novel for the greater part. If necessary, they may be obtained in a manner known for the preparation of analogous compounds.

Compounds of formula 1 which possess an alkoxy group at the 6'-position and wherein $R^3$ is vinyl, are preferably converted to the corresponding 6'-hydroxy compounds with boron tribromide, which compounds may be converted in the same or another 6'-alkoxy compound in conventional manner, preferably with the aid of a mesyl ester. The 6'-alkoxy compounds in which $R^3$ is ethyl, may be also converted with 48% hydrobromic acid to 6'-hydroxy compounds.

The reaction products obtained may be isolated from the reaction mixture and purified by conventional means.

In a number of cases, certain reaction steps may be carried out in a different sequence or simultaneously or without isolating intermediates, and these possibilities are all included in the invention.

Those skilled in the art will appreciate that protecting groups may be used to protect certain reactive functions during the above processes, in accordance with conventional chemical practice.

Certain compounds of formula 1 may also be used for the preparation of other compounds of formula 1 and are therefore also suitable as intermediates.

Diastereoisomers may be separated by known techniques, based on their different physical and chemical characteristics, e.g. by fractional crystallization or by column chromatography. These isomer separations may be effected after the final step of the synthesis used or optionally at a previous stage, after the formation of the mixture of diastereoisomers.

The free base and acid addition salt forms of the compounds of formula 1 may be interconverted by standard methods.

The compounds of formula 1 possess pharmacological activity. In particular they possess cardiovascular activity, for example anti-hypertensive, anti-thrombotic, vasodilatory and anti-arrhythmic activity.

An indicated suitable daily dosage (for a 70 kg human) is from 1 to 200 mg, of a compound of formula 1, preferably administered orally or parenterally in divided dosages of from 0,5 mg to 50 mg 2 to 4 times daily, or in retard form. Unit dose forms for administration may thus contain 0.5, 1, 2.5, 5, 10, 20, 25 or 50 mg of an active ingredient.

The compounds may be administered in free base form or in the form of their pharmaceutically acceptable acid addition salt forms, which salt forms have the same order of activity as the free base forms.

The compounds of formula 1 may be admixed with conventional pharmaceutically acceptable diluents or carriers. If desired, other excipients may be added to facilitate adminsitration, for example in such forms as tablets, capsules and injectable solutions. The compounds may be administered in combination preparations with other active agents.

The pharmaceutical compositions may be formulated in conventional manner, e.g. as for other anti-hypertensive or anti-arrhythmic agents.

The following Examples illustrate the invention.

EXAMPLE 1

2'-Methoxyhydrocinchonicinol-2 dihydrate

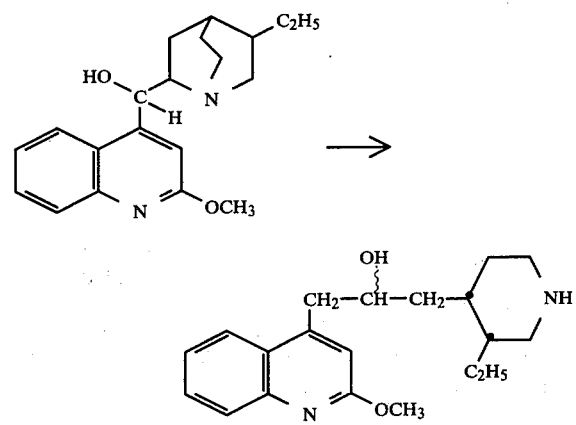

2'-Methoxyhydrocinchonidine, 9,8 g (30 mmol), which was obtained in the same way as the corresponding known 2',6'-dimethoxyhydrocinchonidine, was dissolved in 50 ml of absolute ethylalcohol, after which 5,6 g (33 mmol) of benzyl bromide was added. The mixture was refluxed for 6 hours, after which the conversion into the quaternary salt was found complete. The reaction mixture was poured into water and extracted twice with 100 ml of chloroform. After drying and evaporation in vacuo the quaternary salt was obtained, which was then dissolved in 50 ml of 96% ethylalcohol. To this solution 100 ml of 10% potassium hydroxide was added. The mixture was refluxed for 1 hour giving rise to the N-benzyl-2'-methoxyhydrocinchonicine-1,2-epoxide. The mixture was poured into water, after which the oxirane was extracted twice with 100 ml of ethyl acetate. The collected fractions were dried over magnesium sulphate, filtered and evaporated to dryness in vacuo, affording the oxirane as an oil.

The resulting oil was dissolved in 75 ml of absolute ethylalcohol, to which 2 g of palladium (5%) on active coal were added. Then hydrogen gas was led through the solution. After 650 ml of hydrogen were taken up in the first instance at room temperature and at atmospheric pressure, another 550 ml of hydrogen were taken up after heating to 60° C. The reaction mixture was filtered and evaporated in vacuo to dryness. The resulting crude product was dissolved in chloroform and purified with column chromatography (silica gel/toluene-methanol 10:1). After evaporation in vacuo, crystallization and recrystallization from cyclohexane the 2'-methoxy-hydrocinchonicinol-2 was obtained as its dihydrate. Melting point 198°-199° C.

EXAMPLE 2

2'-Methoxy-hydroquinicinol-2

In the same way as described in Example 1 but starting with 2'-methoxy-hydroquinine instead of 2'-methoxyhydrocinchonidine the title compound was obtained as an oil.

EXAMPLE 3

2'-Hydroxy-desoxo-hydrocinchonicine.bioxalate

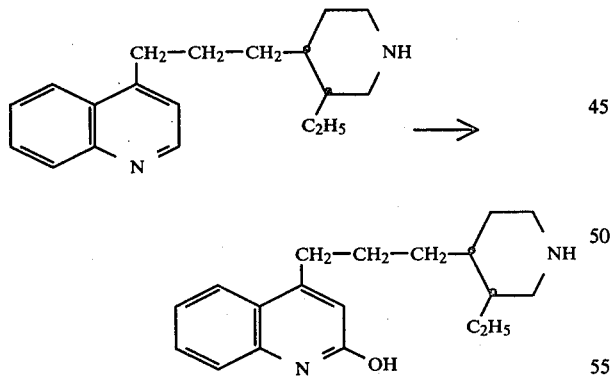

Desoxo-hydrocinchonicine bioxalate (20 g) with a melting point of 156°-158° C. was suspended at room temperature in 100 ml of absolute alcohol. To this suspension 32,7 g m-chloroperbenzoic acid, dissolved in 50 ml of absolute alcohol were added dropwise in 1 hour in such a way that the temperature of the reaction mixture did not exceed 45° C. After it was found by thin layer chromatography that the starting compound was substantially completely converted, SO2 gas was introduced under cooling till no more peroxide could be traced. The mixture was evaporated to dryness in vacuo, after which 100 ml of 1 N hydrochloric acid were added. After filtrating the m-chlorobenzoic acid the filtrate was brought to pH 10 with concentrated ammonia. The desoxo-hydrocinchonicine-N-oxide was extracted three times with 100 ml of chloroform, after which the compound was obtained as an oil after evaporation to dryness in vacuo.

The resulting product was dissolved in 75 ml of chloroform, after which 16.2 g phosphorus oxychloride, dissolved in 50 ml of chloroform were added. The mixture was refluxed for 1.5 hour, during which gaseous hydrochloric acid escaped. The reaction mixture was then cooled and poured onto a mixture of concentrated ammonia and ice. The formed 2'-chloro-desoxo-hydrocinchonicine was extracted three times with 100 ml of chloroform. The crude product was purified with column chromatography (silica gel/chloroform). After evaporation to dryness in vacuo the 2'-chloro-desoxo-hydrocinchonicine was obtained as an oil.

The obtained product was dissolved in 100 ml of 4 N sulphuric acid. The reaction mixture was refluxed for 4 hours and the conversion was followed by thin layer chromatography. After it was found that the starting product was substantially completely converted, the mixture was cooled and poured into a mixture of concentrated ammonia and ice. The organic material was extracted three times with 100 ml of chloroform at pH 10. After purification by column chromatography (silica gel/chloroform-methanol 10:1) and evaporation to dryness the 2'-hydroxy-desoxo-hydrocinchonicine was obtained as an oil. The oil was dissolved in 50 ml of methyl ethyl ketone, to which an equivalent amount of oxalic acid was added. After crystallization and recrystallization the 2'-hydroxy-desoxo-hydrocinchonicine bioxalate was obtained. Melting point 198°-200° C.

EXAMPLE 4

2'-Hydroxy-desoxo-hydroquinicine.bioxalate

In the same way as described in Example 3 the title compound was prepared starting with desoxo-hydroquinicine. The melting point of the bioxalate was 196°-198° C.

EXAMPLE 5

1-(2-Trifluoromethyl-4-quinolyl)-3-[3(R)-ethyl-4(S)-piperidyl]-propanone-2 bifuamarate

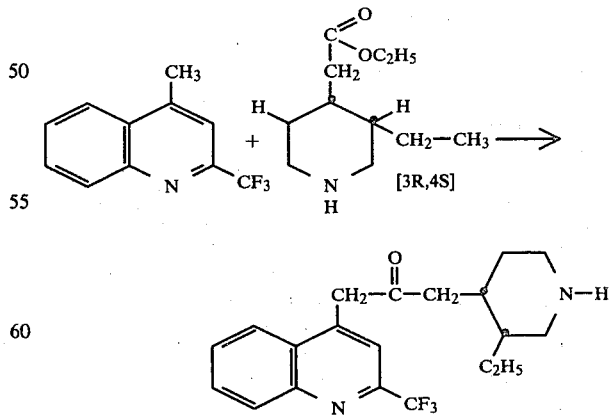

To 75 ml (124.2 mmol) of 15% n-butyllithium in hexane at −70° C. 21 ml (123 mmol) of diisopropylamine were added in 20 min. with stirring and in a nitrogen atmosphere. Then 23.6 g (111.8 mmol) of 4-methyl-2- trifluoromethylquinoline in 80 ml of tetrahydrofuran were added in 45 minutes at −70° C., followed by 14.5 g (72.9 mmol) of [3(R)-ethyl-4(S)-piperidyl]-acetic acid ethyl ester in 80 ml of tetrahydrofuran in 30 min. The reaction mixture was stirred for 2 hours at −70° C. and for 3 hours at −25° C. The reaction mixture was acidified with acetic acid to pH 6, after which 8.5 g of potassium bicarbonate were added. Then the reaction mixture was left over night at room temperature.

The reaction mixture was diluted with 150 ml of methanol, filtered and evaporated to dryness in vacuo. To the residue 200 ml of water were added and 4 N hydrochloric acid was added to pH 4. Subsequently the mixture was extracted with ether (total amount 500 ml).

The water phase was made alkaline with concentrated ammonia to pH 8–9 and extracted with chloroform (total amount 300 ml). The chloroform extract was dried over magnesium sulphate, filtered and evaporated to dryness in vacuo.

The resulting crude 1-(2-trifluoromethyl-4-quinolyl)-3-[3(R)-ethyl-4(S)-piperidyl]-propanone-2 was purified with the aid of HPLC (Silica Gel with chloroform-:acetone:diethylamine 5:4:1). The yield of pure product (oil) is 44.5%. The base was converted with fumaric acid to the bifumarate (mol. ratio 1:1) with a melting point of 140° C.

EXAMPLE 6

1-(2-Methoxy-4-quinolyl)-3-[3(R)-ethyl-4(S)-piperidyl]-propanone-2

In the same way as described in Example 5, but starting with 2-methoxy-4-methylquinoline instead of 4-methyl-2-trifluoromethylquinoline, the title compound was obtained as an oil.

EXAMPLE 7

1-(2-Trifluoromethyl-4-quinolyl)-3-[3(R)-ethyl-4(S)-piperidyl]-propanol-2 bifumarate

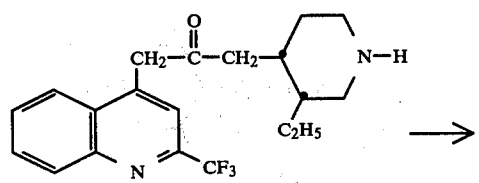

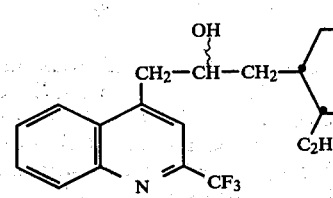

Sodiumborohydride, 2.2 g (60 mmol) was suspended with stirring of 50 ml in isopropanol.

A solution of 10.6 g (29.0 mmol) of 1-(2-trifluoromethyl-4-quinolyl)-3-[3(R)-4(S)-piperidyl]-propanone-2 (Example 5) in 50 ml of isopropanol were then added at −5° C. in 45 minutes. The reaction mixture was stirred for 45 minutes at −5° C. and diluted with 200 ml of water.

The mixture was extracted with chloroform (total amount 450 ml).

The chloroform extract was dried over magnesium sulphate, filtered and evaporated to dryness in vacuo. The yield of the mixture of isomers of 1-(2-trifluoromethyl-4-quinolyl)-3-[3(R)-ethyl-4(S)-piperidyl]-propanol-2 was 90%.

By means of column chromatography with silica gel and chloroform/methanol/diethylamine (80:5:10) as eluent these isomers were separated and both converted to their bifumarate salts with 1 quivalent of fumaric acid.

Isomer-1 had a melting point of 149°–150° C. and isomer-2 of 190°–191° C.

EXAMPLE 8

2′-Hydroxy-hydrocinchonicinol-2

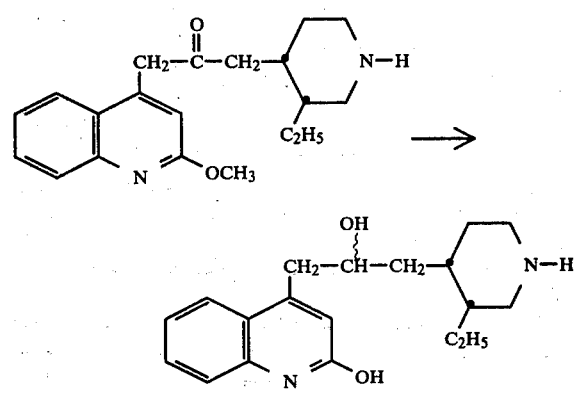

A mixture of 1.0 g (3.1 mmol) of 1-(2-methoxy-4-quinolyl)-3-[3(R)-ethyl-4(S)-piperidyl]-propanone-2 (Example 6) in 10 ml of 47% HBr-solution was warmed at 105° C. for 3 hours. After cooling to room temperature the reaction mixture was basified (pH 9) with concentrated ammonia and extracted with chloroform. The chloroform extract was dried over magnesium sulphate, filtered and evaporated in vacuo. The obtained crude 1-(2-hydroxy-4-quinolyl)-3-[3(R)-ethyl-4(S)-piperidyl]-propanone-2 was converted into the title compound in the same way as described in Example 7. The compound was obtained as an oil.

EXAMPLE 9

2′-Trifluoromethyl-desoxo-hydrocinchonicine

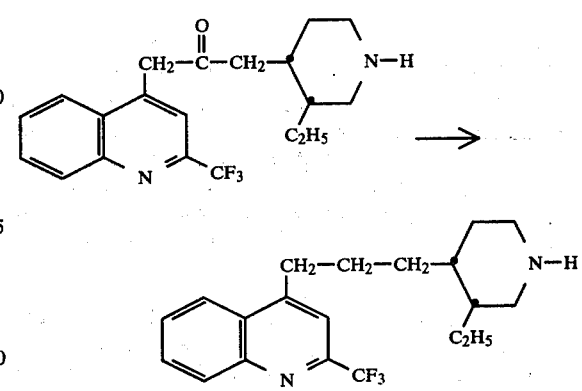

1-(2-Trifluoromethyl-4-quinolyl)-3-[3(R)-4(S)-piperidyl]-propanone-2 (Example 5), 5.0 g (13.7 mmol), was dissolved in 17 ml of ethylene glycol, after which 1.7 ml of 80% hydrazine hydrate were added. The mixture was heated till 140°–150° C. in a nitrogen atmosphere, and water was removed during 2 hours with a Dean-Stark apparatus. Then 2.3 g of potassium hydroxide were added to the reaction mixture in about 30 minutes, which caused evolution of nitrogen. After the addition of potassium hydroxide was completed, the mixture was heated at 140° C. for another 3 hours. After cooling to about 70° C. the mixture was poured into 100 ml of water, after which the product was extracted twice with 100 ml of chloroform. The collected chloroform fractions were dried over magnesium sulphate, filtered and evaporated to dryness in vacuo. The crude product was purified by means of column chromatography over silica gel with chloroform/acetone/diethylamine (5:4:1) as eluent.

The yield of 2'-trifluoromethyl-desoxo-hydrocinchonicine, which was obtained as an oil, was 1.7 g.

PHARMACOLOGY

Experiment 1—Effectiveness of the compounds of Examples in spontaneously hypertensive rats Systolic blood pressures were recorded by a modification of the tail cuff method described by I. M. Claxton et al, Eur. J. Pharmacology 37, 179 (1976). An oscilloscope or W+W BP recorder, model 8002, was used to display pulses.

Prior to all measurements rats were placed in a heated environment (33.5°±0.5° C.) before transfer to a restraining cage. Each determination of blood pressure was the mean of at least 6 readings.

Spontaneously hypertensive rats (aged 12–18 weeks) with systolic blood pressures >170 mm Hg were considered hypertensive.

In de following table the results with certain compounds of the invention, which have been carried out with the above-described method, are mentioned. The numbers of the compounds correspond with those of the Examples.

| Compound No. | dosage mg/kg | change of systolic blood pressures (%) in different time intervals (h) | | | | |
|---|---|---|---|---|---|---|
| | | 1 | 2 | 4 | 6 | 24 |
| 1 | 10 | −11 | −1 | +1 | −4 | — |
| 3 | 10 | −10 | −11 | −12 | −6 | — |
| 7-1 | 10 | +3 | +4 | +1 | −3 | +4 |

Experiment 2—Effectiveness of the compounds of Examples in the Guinea Pigs Electrostimulation Test Arrhythmias are induced in guinea pigs by electrostimulation of the right ventricle of the heart. The animals are anesthesized with urethane (1.2 g/kg i.p.) and artificially respirated before a needle electrode is inserted in the right ventricle of the heart. Substances are given intraduodinally 30 min. before the stimulation at a dose as set forth in the following table.

The voltage needed for induction of extra systoles in control animals (n=6) is compared with that required for induction of arrhythmias in treated animals (n=6). This method is based on the work of L. Szekeres and G. J. Papp, Naunyn-Schmiedebergs Arch. Exp. Path. Pharmak., 245, 70 (1963).

In the table the results of certain compounds of the invention are mentioned, which have been carried out according to the method described above.

The numbers of the compounds correspond with those of the Examples.

| Compound No. | Percent increase in voltage required for arrhythmia |
|---|---|
| 1 | 44 (16 mg/kg) |
| 3 | 94 (32 mg/kg) |
| 4 | 31 (16 mg/kg) |
| 7-1 | 57 (4 mg/kg) |
| 7-2 | 57 (8 mg/kg) |

TOXICOLOGY

The compounds did not cause toxic signs at the doses used for the different tests.

We claim:

1. A compound of the formula

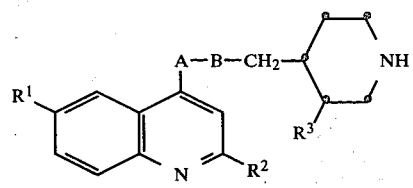

or a pharmaceutically acceptable salt thereof in which
A–B is —CH₂—CH₂—, —CHOH—CH₂—, —CH₂—CHOH—, —C(O)—CH₂—, —CH₂—C(O)—, —C(NOR⁴)—CH₂— or —CH₂—C(NOR⁴)—,
R¹ is hydrogen, hydroxy or lower alkoxy,
R² is hydroxy, lower alkoxy or trifluoromethyl,
R³ is ethyl or vinyl, and
R⁴ is lower alkyl,
in which the configuration of the substituents in the 3- and 4-position of the depicted piperidine ring is cis.

2. A compound according to claim 1 wherein A–B is —CH₂—CH₂—, —CHOH—CH₂—, —CH₂—CHOH—, —C(NOR⁴)—CH₂— or —CH₂—C(NOR⁴)—, in which R⁴ is lower alkyl.

3. A compound having the formula

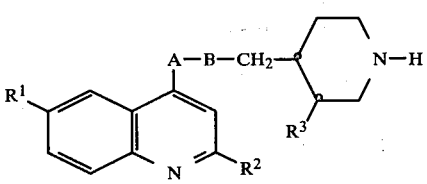

or a pharmaceutically acceptable salt thereof, in which
A–B is —CH₂—CH₂—, —CHOH—CH₂—, —CH₂—CHOH—, —C(O)—CH₂—, —CH₂—C(O)—, —C(NOR⁴)—CH₂— or —CH₂—C(NOR⁴)—,
R¹ is hydrogen, hydroxy or lower alkoxy,
R² is hydroxy or lower alkoxy,
R³ is ethyl or vinyl, and
R⁴ is lower alkyl,
in which the configuration of the substituents in the 3- and 4- position of the depicted piperidine ring is cis.

4. The compound according to claim 3, wherein A–B is —CH₂—CHOH and R² is lower alkoxy.

5. The compound according to claim 3, wherein A–B is —CH₂—CH₂— and R² is hydroxy.

6. A compound according to claim 1 wherein A–B is —CH₂—C(O)— or —CH₂—CHOH—;
R² is trifluoromethyl; and
R¹ and R³ are as therein defined.

7. A compound according to claim 1 wherein

A–B is —C(NOR$^4$)—CH$_2$— or —CH$_2$—C(NOR$^4$)— and

R$^1$, R$^2$ and R$^3$ are therein defined.

8. A pharmaceutical composition comprising a cardiovascularly effective amount of a compound according to claim 1, or a pharmaceutically acceptable salt thereof, in combination with a pharmaceutically acceptable carrier.

9. The compound according to claim 3 wherein

R$^1$ is hydrogen,

R$^2$ is methoxy, and

R$^3$ is ethyl.

10. The compound according to claim 9 wherein

R$^1$ is hydrogen or methoxy and

R$^3$ is ethyl.

11. A compound according to claim 6 wherein

A–B is —CH$_2$CHOH—,

R$^1$ is hydrogen and

R$^3$ is ethyl.

12. A compound according to claim 11 in a substantially pure single diastereoisomer form.

13. A mixture of two diastereoisomers of a compound according to claim 12.

14. The method of treating cardiovascular conditions in a human or other animal in need thereof which comprises administering an effective amount of a compound according to claim 1.

\* \* \* \* \*